United States Patent
Ehbets et al.

(10) Patent No.: US 7,679,785 B2
(45) Date of Patent: Mar. 16, 2010

(54) METHOD FOR CORRECTING MEASURED IMAGE VALUES

(75) Inventors: Peter Ehbets, Zürich (CH); Adrian Kohlbrenner, Thalwil (CH); Harald Ammeter, Zürich (CH)

(73) Assignee: X-Rite Europe GmbH, Regensdorf (CH)

( * ) Notice: Subject to any disclaimer, the term of this patent is extended or adjusted under 35 U.S.C. 154(b) by 469 days.

(21) Appl. No.: 11/666,369

(22) PCT Filed: Oct. 28, 2005

(86) PCT No.: PCT/EP2005/011591

§ 371 (c)(1),
(2), (4) Date: Apr. 26, 2007

(87) PCT Pub. No.: WO2006/045620

PCT Pub. Date: May 4, 2006

(65) Prior Publication Data

US 2007/0260413 A1 Nov. 8, 2007

(30) Foreign Application Priority Data

Oct. 28, 2004 (EP) .................................. 04025620
Feb. 16, 2005 (CH) .................................... 0264/05

(51) Int. Cl.
*H04N 1/028* (2006.01)
*G01J 3/46* (2006.01)
(52) U.S. Cl. .................. 358/1.9; 358/406; 358/504; 356/402
(58) Field of Classification Search ............. 358/1.9, 358/3.24, 3.26, 406, 504; 382/112; 356/402
See application file for complete search history.

(56) References Cited

U.S. PATENT DOCUMENTS

| | | | |
|---|---|---|---|
| 4,449,147 A | 5/1984 | Ogasawara | |
| 4,575,249 A | 3/1986 | Grieger | |
| 5,554,432 A | 9/1996 | Sandor et al. | |
| 6,028,682 A | 2/2000 | Ott et al. | |
| 6,535,279 B1 | 3/2003 | Lampersberger et al. | |

FOREIGN PATENT DOCUMENTS

EP 1154247 11/2001

OTHER PUBLICATIONS

PCT International Search Report dated Feb. 6, 2006.

*Primary Examiner*—Scott A Rogers
(74) *Attorney, Agent, or Firm*—McCarter & English, LLP

(57) ABSTRACT

Image measurement values of a measurement object, in particular a printed sheet, measured by means of a photoelectric image measuring unit operating on the basis of pixels are corrected with respect to at least one influencing variable which influences the measurement result with a view to at least partially eliminating the effect of this influencing variable on the measuring process. The image measurement values measured by the image measuring unit are converted by correction parameters of a parameter-based correction model into corrected image measurement values which no longer contain the influencing variable affecting the measuring process. The correction parameters used for the parameter-based correction model are automatically calculated using reference measurement values measured at reference measurements points on preferably the same measurement object by means of a reference measuring unit and the image measuring unit. In particular, image measurement values measured without polarization filters are converted into polarization filter image measurement values by means of this method. Influences induced by print medium, fluorescence effects and the influences of non-standard measuring geometries are also corrected.

19 Claims, 6 Drawing Sheets

METHOD FOR CORRECTING MEASURED IMAGE VALUES

FIELD OF THE INVENTION

The invention relates to a method of correcting image measurement values of a measurement object obtained by means of a photoelectrically operating image measuring system on the basis of image pixels, in particular a printed sheet.

BACKGROUND ART

These days, color and density measurement values of printed sheets are often detected by means of a multi-channel measuring method operated in parallel. A multi-channel, measuring method operated in parallel is referred to as an image measuring technique below because it is typically used to detect the measurement data of a whole image or a section of an image on the basis of image pixels. With the age of digital processing, ever increasing importance is being ascribed to the availability of image measurement values and the direct use of digital data from the preliminary processing stage for controlling printing machines. Image measurement values permit efficient quality control of the printed product and are also used for color control and color regulation in the image.

Known methods may be used to detect image measurement values (on the basis of image pixels). One known option is the camera measuring method. It is used in roller printing machines, in digital printing machines and also in sheet offset printing machines as a means of monitoring quality. Line cameras are known, which detect one image line after the other, parallel in sequence. Alternatively, two-dimensional camera systems are used, which detect a limited two-dimensional image field in parallel and compile larger image fields from several measurements with a mechanical offset. Examples of the camera measuring system used in printing machines are the products made by Eltromat GmbH. A specific example is disclosed in patent application EP1213569A2, which describes a camera system specially designed for color measuring systems.

As an alternative to imaging systems, commercially available scanners may be used, in which case the printed sheet is placed on a support and scanned sequentially by a measuring beam. In the simplest approach, the measuring unit of a commercially available flat-bed scanner may be used. Measurement data of better quality can be obtained by using a system specifically optimized for measuring color. Such systems are described in patent U.S. Pat. No. 6,028,682 (≈DE-A 196 50 223) or in this patent application, for example.

If image measurement values are to be used for color applications or density measurements, the image measurement values must be converted into the corresponding variables. The conversion is referred to as colorimetric calibration and can be run in a known manner. A correction matrix is preferably determined by means of a compensating calculation using reference measurement values, which transforms the image measurement values into the desired units (standard color values CIE XYZ or density filter values).

The image measurement values are usually RGB values, multi-filter measurement values (more than 3 measurement values per image pixel) or spectral measurement data (per image point or pixel). As a rule, the colorimetric measuring accuracy of the system is increased, the more different spectral measurement values there are per image pixel or the more accurately the filter functions of the measuring system are adapted to the desired evaluation filters (for example the colorimetric normal observer functions or the density filter functions).

Colorimetric calibration alone is not sufficient for the application of imaging technology in the printing industry. The measuring performance of the system is also affected by process parameters of the printing process and factors dependent on the print medium used.

One known problem is the wet-dry problem which primarily causes difficulties with regard to the measuring technology used in the offset printing method. The printer must be able to test the print quality during the printing operation. At this point in time, the ink applied is still fresh, however. The color coating on the substrate is wet and exhibits a strong sheen. During the drying process, the color coating conforms to the structure of the substrate surface, which reduces the sheen and causes significant changes in the measurement values over time (during the drying phase), especially in the case of mat papers.

The difference between measurement values taken on wet and dry substrate can be reduced using the known polarization filter measuring method. With this measuring method, the sample is illuminated with polarized light and a polarization filter orthogonal to the polarization direction of the illuminating light is used as an analyzer in the collection channel. Orthogonal polarization filters eliminate the component in the measurement light which is reflected from the surface and represents the variable part.

The polarization filter measuring method is primarily used for measuring density and is integrated in commercially available manual measuring systems, such as the spectral photometer, SpectroEye, sold by GretagMacbeth, for example. To date, the polarization filter measuring method has not been used in image-producing color measuring systems for controlling printing processes. The reason for this is that process control systems must be able to take measurements quickly and the orthogonal polarization filters cause a light loss based on a factor of 8 to 10, which has to be compensated by correspondingly longer measuring times, which would be too long for controlling the printing processes. For this reason, patent U.S. Pat. No. 6,028,682 (≈DE-A 196 50 223), for example, describes image measuring systems which are not equipped with polarization filters.

In many applications, however, the measuring system is required to output density values based on the polarization filter measuring method. Furthermore, the polarization filter measuring method offers better linearity of the measurement values as a function of changes in coating thickness and does so when calorimetrically characterizing samples with high densities, such as occur in the case of highly pigmented inks, for example. The polarization filter measuring method would therefore also improve calorimetric regulation of the ink applied by the printing machine possible.

In known measuring systems, such as that described in patent U.S. Pat. No. 6,028,682 (≈DE-A 196 50 223), polarization filter density values are calculated using a correction model using measurement values taken without polarization filters. The correction model operates with fixed parameters. As input variables for the model, the printer can select from a limited number of paper qualities (substrates) only. The relevant correction parameters for these paper qualities are determined on the basis of experiments conducted beforehand. In its simplest form, the correction model corresponds to the subtraction of an offset value from the reflectance value measured without polarization filters. However, the quality obtained on the basis of the correction is not satisfactory. The accuracy of the correction is limited by the large number of different printing substrates with different surface properties. The limited set of typical paper qualities can not emulate this multiplicity. Furthermore, the model is particularly inaccurate with the offset correction for use at high densities and the implementation does not contain sufficient parameters for use with spectral or colorimetric measurement values. Measurement values in the absorption range, at the sides or in the transmission range of a spectrum exhibit various differences depending on whether the measurements are taken with or without polarization filters, which demands a more complex correction model.

The different surface properties of the print samples also cause problems with regard to the measuring geometry. In image measuring methods, it is often not possible to preserve the measuring angle (i.e. 45°/0°-measuring geometry) prescribed for calorimetric methods sufficiently accurately for various reasons. Variations in angle cause differences in the measurement values compared with a color measuring device of standard geometry. However, the differences in the measurement values are also dependent on the paper quality used. Characterizing the measurement differences during manufacture of the device and then running a fixed programmed correction is therefore not good enough for subsequent application using different substrates (paper qualities).

Another problem is the fact that image measuring systems are often designed on a line-oriented basis, such as the system described in U.S. Pat. No. 6,028,682 (≈DE-A 196 50 223), for example. In this case, lighting can be applied from only one angular direction for geometric reasons. In samples with a rough surface, this constraint results in measurement errors induced by direction, depending on how the sample is oriented underneath the measuring device. The color differences induced by direction may be greater than dE*ab=5 on natural paper and the corresponding density variances are greater than 10%. These tolerances are unacceptable for many applications or at least cause problems.

SUMMARY OF THE INVENTION

An objective of this invention is to propose a solution to these known problems and enable a simple image measuring method or any color measuring system of simple design to be used for qualified process and color control during printing operations and thus reduce disruptive effects induced by media and geometry.

More specifically, the intention of this invention is to permit a basic improvement in correcting image measurement values to obtain measurement values conforming to the polarization filter measuring method. The correction should be applied not just to the density values, but to the entire reflectance spectrum. Furthermore, additional measurement differences caused by variances in the measuring geometry or due to the disposition of the lighting system should be compensated.

The invention provides a method of correcting image measurement values of a measurement object determined by means of a photoelectrically operating image measuring unit on the basis of image pixels, in particular a printed sheet, in respect of at least one influencing variable which influences the measurement results with a view to at least partially eliminating the effect on the measuring process induced by this at least one influencing variable, whereby the image measurement values measured by means of the image measuring unit are converted by correction parameters of a parameter-based correction model into corrected image measurement values which do not contain at all or only at least partially contain the effects on the measuring process induced by the influencing variable, wherein the correction parameters used for the parameter-based correction model are determined from reference measurement values measured at selected reference measurement points of preferably the same measurement object by means of a reference measuring unit and the image measuring unit, and a reference measuring unit is used which is not susceptible to the at least one influencing variable or the latter has no or only a negligible effect on the measuring process.

In accordance with the principle of the invention in the most general sense, the corrections are applied using a parameter-based model, and the correction parameters used in the model are determined from reference measurement values on the same medium (substrate), preferably taken automatically and without additional input.

BRIEF DESCRIPTION OF THE DRAWINGS

The invention will be explained in more detail with reference to the drawings. Of these.

DETAILED DESCRIPTION OF THE PREFERRED EMBODIMENT

FIGS. 1-4 illustrate a preferred embodiment of the scanning device. In terms of its general construction, it corresponds to standard measuring apparatus, of the type typically used in the graphics industry for photoelectrically measuring printed sheets during a printing process on the basis of pixels, for example. Such printed sheets are also be referred to as measurement object or sample in the following description.

Figure 1:
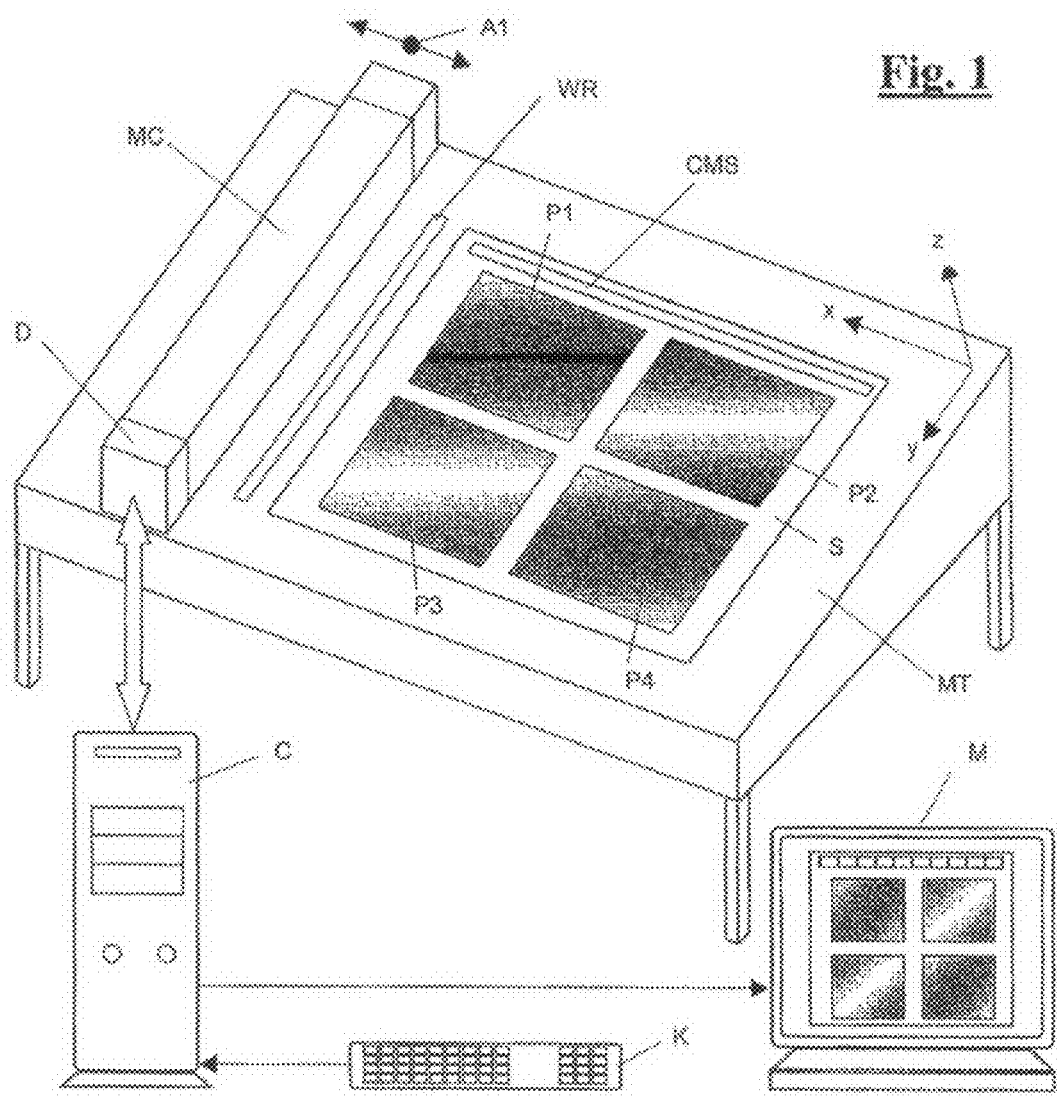
FIG. 1 is a simplified overall view of a scanning device that is particularly suitable for the purpose of the invention.
Figure 2:
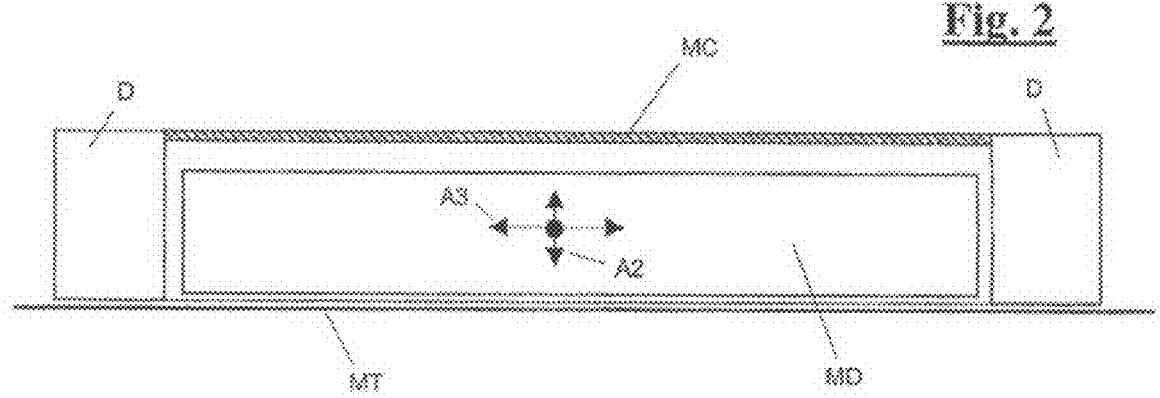
FIG. 2 is a partial longitudinal section parallel with the y-z co-ordinate plane through the measuring carriage of the scanning device.

The scanning device comprises a sub-structure in the form of a measuring table MT with a usually inclined rectangular surface on which the measurement object S—the printed sheet to be measured—can be positioned. The printed sheet S typically contains various (in this example four) graphic illustrations P1-P4 and a (or several) color measuring strip CMS. In order to position the measurement object S, stops are provided on the measuring table MT, although these are not illustrated. The measurement object S is preferably secured on the measuring table MT by electrostatic means or by means of known suction mechanisms. Disposed on the measuring table MT is an elongate measuring beam or measuring carriage MC, on or in which a measuring device MD (FIG. 2)

is disposed. The measuring carriage MC extends across the depth of the measuring table MT in the direction of the y co-ordinate and can be moved linearly backwards and forwards across its width in the direction of the x co-ordinate, driven by motor, for which purpose appropriate drive and control devices are provided on the measuring carriage MC and on or underneath the measuring table MT. The drive system is symbolically indicated by reference D in the drawing and the movement of the measuring carriage MC in the x direction is indicated by arrow A1. Disposed inside the measuring carriage MC is the actual measuring device MD which can be raised and lowered in the direction of the co-ordinate axis z relative to the measuring table surface and, in certain embodiments, also in the direction of the y co-ordinate axis (to a limited degree) by means of which conventional drive systems, not illustrated. These two possible movements are symbolized by arrows A2 and A3 in FIG. 2.

Disposed on the measuring table MT parallel with the measuring carriage MC is a white reference WR. It is used for calibrating the measuring device MD. The calibration is usually run prior to every measuring routine by the measuring device MD, which measures the white reference. The white reference was measured previously (usually at the factory) with the aid of an external device and the measurement values stored in the memory of the scanning device, as a rule in the computer C. Such a calibration is standard practice when using spectral photometers and as such is prior art.

The scanning device also comprises a processing unit in the form of a (possibly also external) computer C with a keyboard K and a color monitor M. The computer C co-operates with a measurement and drive control system on the measuring table MT or in the measuring carriage MC, although this is not illustrated here, and processes the measurement signals generated by the measuring device MD disposed in the measuring carriage MC and forwarded to it via the measurement and drive control system MDC, and amongst other things is also able to display the image data of the scanned measurement object S on the monitor M. The computer C can also command and control the measurement and drive control system in order to move the measuring carriage MC and the measuring device MD disposed in it. To this extent, the scanning device corresponds to the prior art, as known from the devices sold by Heidelberger Druckmaschinen AG or as specified in U.S. Pat. No. 6,028,682 (corresponding to DE-A-196 50 223), for example. The mechanical construction and the implementation of the motor-driven movements of the measuring carriage MC and measuring device MD are described in detail in patent U.S. Pat. No. 6,028,682 and the skilled person therefore requires no further explanation in this respect. It goes without saying that the measuring carriage MC may also be disposed parallel with the co-ordinate direction x, in which case all other orientations and directions of movements would likewise be rotated accordingly by 90°.

The most essential components of the measuring device MD disposed in the measuring carriage MC are a lighting system for illuminating the measurement object, optical pickup means for picking up the measurement light reflected by the measurement object and a wavelength range selective, photoelectric receiver device for converting the reflected measurement light into electric measurement signals. These elements are used for scanning the entire printed sheet on the basis of pixels and will be referred to as a whole as image measuring unit.

Figure 3:
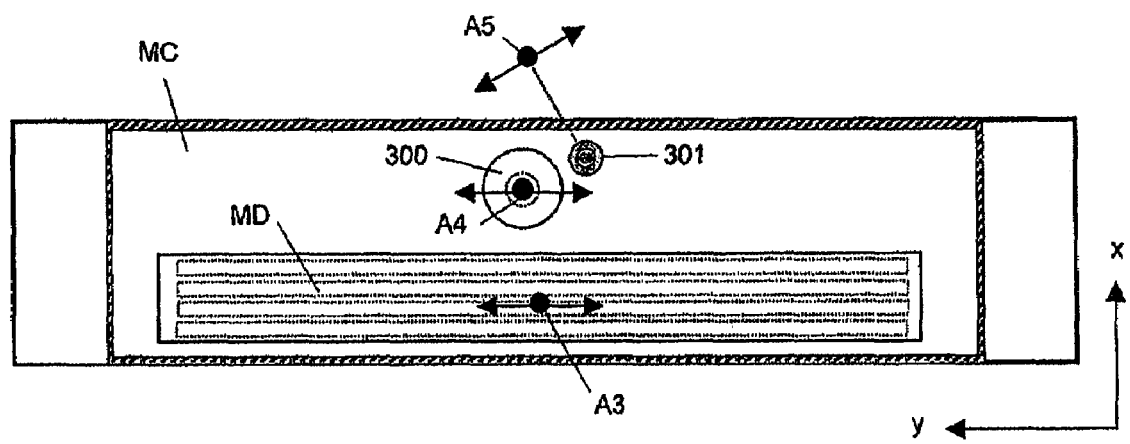
FIG. 3 is a partial longitudinal section parallel with the x-y co-ordinate plane through the measuring carriage of the scanning device.

In addition to said image measuring unit, the measuring device MD is also equipped with an independent spectral measuring head for taking spectral measurements of individual image elements, as schematically indicated in FIG. 3.

This spectral measuring head 300 can be moved in the y direction separately from the other components of the measuring device by means of a motorized drive indicated by arrow A4 in the drawing and can therefore be positioned above every image element of the measurement object in conjunction with the movement of the measuring carriage MC in the x direction. The spectral measuring head 300 and its drive in the y direction is naturally also controlled by the measuring and control system. The spectral measuring head 300 is equipped with a polarization filter 301, which can be introduced into the measurement optical path and moved back out of it again by remote control, so that spectral measurements may be taken selectively with and without polarization filter. The movement of the polarization filter 301 is symbolized by arrow A5 in FIG. 3. The polarization filter 301 comprises two concentric parts, the polarization directions of which intersect one another. The lighting optical path extends through the outer part, whilst the measuring light optical path extends through the inner part. To enable measurements to be taken with different filters at the same time, it is also possible to provide more than one independent spectral measuring head, for example in order to obtain measurements with two spectral measuring heads with and without a polarization filter.

In practical application, the spectral measuring head 300 is used for high-precision (spectral) measurements on relatively few selected image elements of the measurement object S. It is typically used to measure the color control strip CMS (FIG. 1) provided as standard on printed sheets. This may be done in a separate scanning pass or alternatively together with the or one of the scanning passes of the measuring device MD. In both situations, in view of the fact that the exact position of selected image elements is not known a priori, it is of particular advantage if the image data detected by the measuring device with the line sensors is interpreted so that they can be used for positioning the independent spectral measuring head on specific image elements. For example, the exact position of the color control strip CMS can be determined during the measuring operation in particular and as a result, the independent spectral measuring head can be selectively positioned above the relevant image elements.

In terms of quality, the spectral measuring head is a highly precise color measuring system. It satisfies all the demands placed on measuring technology as set out in international standards governing color measuring technology (for example ISO 13655 or DIN 5033). More particularly, the individual spectral measuring head 300 is designed with an annular or circular measuring geometry so that it is not sensitive to the effects of direction when the test sample is rotated underneath the spectral individual measuring head. An example of such a spectral measuring head is the spectral photometer, SpectroEye, made by GretagMacbeth AG, which can be used as a spectral measuring head in the measuring device. It is also of advantage if the spectral measuring head and the image measuring unit have a lighting spectrum in the measuring light without an ultra-violet (UV) element. This characteristic can be achieved by using an edge filter in the optical light system, which suppresses the spectral element in the lighting spectrum below the wavelength of 400 nm. Commercially available absorption filter glasses made by the Schott company, for example, may be used for such filters. Suppressing the UV element makes it easier to correct the measurement data because allowance does not have to be made for the non-linear effects for the different energization of optical brighteners in the substrate. If UV suppression is not used, compensation must be made for the fluorescence effects of the optical brighteners in the correction model.

Ideally, allowance is made for this compensation in a correction model when making allowance for the effect of the measuring geometry and type of medium. Both variants re described in more detail below. The spectral measuring head 300 will also be referred to as reference measuring unit below.

Figure 4:
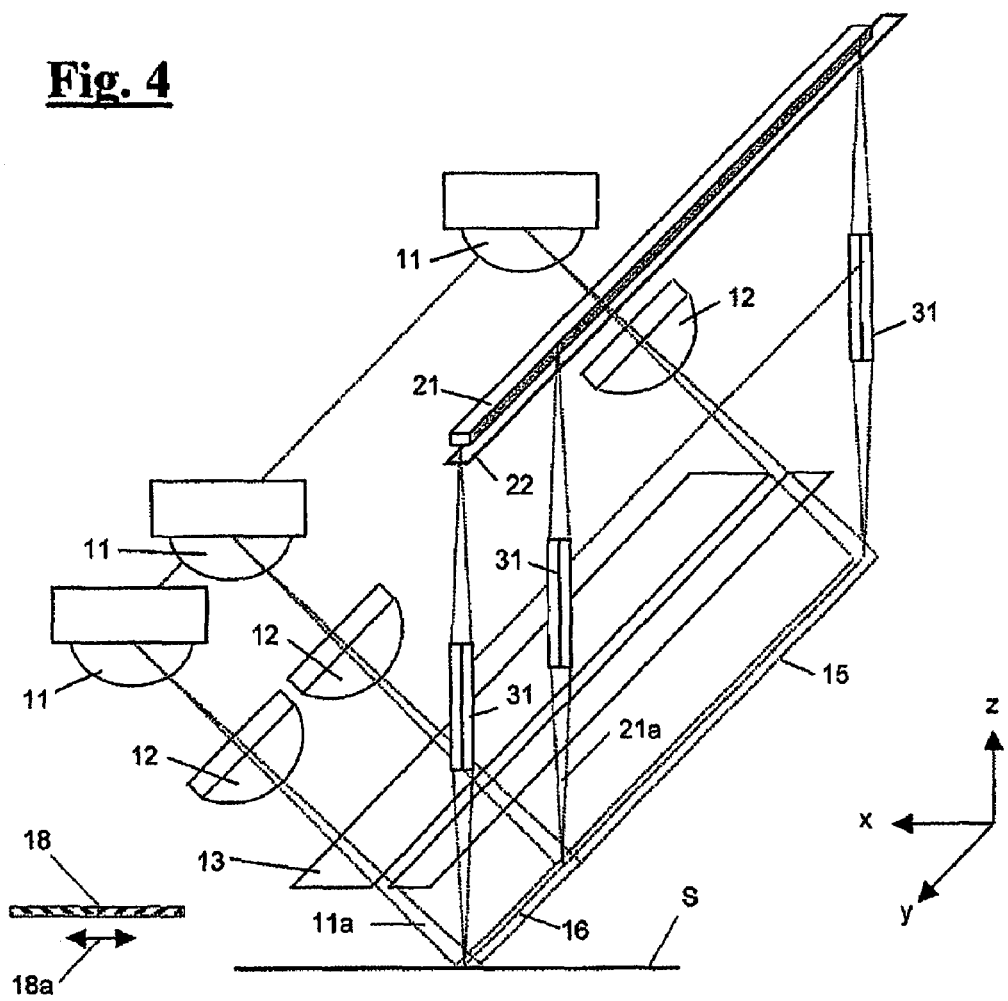
FIG. 4 is an outline of the basic structure of the measuring device disposed in the measuring carriage.

FIG. 4 illustrates the main construction of the image measuring unit of the measuring device MD. The measuring device as a whole constitutes a multi-channel line scanner (as regards wavelength ranges) although only the elements belonging to one color channel (wavelength range) are illustrated in FIG. 4 in order to retain clarity. A full measuring device MD contains several of the configurations illustrated in FIG. 4, disposed in parallel and offset from one another. For example, the measuring device may have six such configurations.

For each color channel the lighting system has a greater number of light sources 11 in the form of light-emitting diodes, which are linearly aligned in a row in the y direction. For each light source 11, it preferably also has a (cylindrical) collimator lens 12 as well as a continuous slot diaphragm 13 extending in the longitudinal direction parallel with the y co-ordinate. The light sources 11 apply illuminating light to the measurement object S within an illuminating strip 15 extending in the longitudinal direction parallel with the y co-ordinate and at least across a part of the measurement object S. The disposition is such that illuminating light is directed onto every image element of the measurement object S to be scanned lying within the illuminating strip 15 at a defined angle of incidence (typically 45°/0°, e.g. DIN 165361, Part 2) appropriate for measuring color. This is achieved by the collimator lenses 12 and the slot diaphragm 13. The collimator lenses 12 create a virtually parallel optical path. The focal distance of the lenses is selected so that the divergence angle of the collimated optical path (in the y direction) is smaller than 5-10°. This implementation permits a largely uniform continuous linear illumination. The optical path of the illumination is indicated by reference 11a in FIG. 4. The slot diaphragm 13 limits the angle of incidence transversely to the longitudinal extension of the illuminating strip, in other words in the direction of the x axis. The light-emitting diodes 11 used may be of the "white" illuminating Luxeon DS 25 type sold by Lumileds Lighting LLC, San Jose, Calif., USA, for example.

The photoelectric receiver unit comprises (for each color channel) a line sensor 21 and a color filter 22 connected upstream, which sensitizes the line sensor to its wavelength bandpass range. The line sensor comprises one or more so-called CIS elements (contact image sensor), each of which in turn has a large number of individual light sensors integrated in a straight line on a chip. A suitable CIS element is that of the P16045J type sold by Peripheral Imaging Corporation, San Jose, Calif., USA with a resolution of 600 dpi, for example.

The optical pick-up means comprise (for each color channel) a linear optical array 31, which is preferably configured as an essentially linear array of gradient index lenses, so-called Selfoc lens arrays. Like the line sensor 21, the linear optical array 31 extends parallel with the y co-ordinate direction. In a typical, commercially available design of a Selfoc lens array 31, two rows of gradient index lenses are disposed between two outer walls, and the gaps between the lens fibers and the walls are cast with an opaque plastic. Suitable Selfoc lens arrays are sold by the NSG company.

The linear optical array 31 directs the reflected measurement light applied to the image elements of the measurement object S by the illuminating light onto the co-operating line sensor 21 (measurement light optical path 21a). The optical array 31 is configured and disposed so that it receives the measurement light reflected by every scanned image element within a defined angle of incidence range suitable for color measurements (typically 0°+/−5°, e.g. DIN 165361, Part 2). The scanned image element line (per color channel) is denoted by reference 16 in FIG. 4.

In practice, it is important to position the slot diaphragm 13 in the optical path of the light as close as possible to the measurement object S. The slot diaphragm 13 limits the illuminated surface on the measurement object. It typically has an aperture width of 1 mm or less. The illuminated surface of the measurement object (illuminating strip 15) therefore has a width (in the x direction) which is shorter than the field of vision of the optical array or Selfoc lens array 31 (in the x direction). This improves suppression of scattered light and allows density measurements to be taken of small measurement fields with a high density in a white environment.

A basic problem of linear illumination is the fact that a point in the measurement field receives light from all the light sources (light-emitting diodes). This being the case, the light from light-emitting diodes offset from the row is no longer oriented at 45° but hits the measurement field at bigger angles. However, the bigger angles do not conform to the standardized color measuring geometry, which only permits an angle of illumination in the range of 40° to 50° (45°+/−5°). Deviations from the standard geometry give rise to measurement errors, which are caused by a different surface effect and by other absorption paths through the color layer.

The effective angle range for the illumination must therefore be limited. This can be done using a plate structure, for example, disposed between the individual light-emitting diodes of a row and the measurement field. However, the plates should not be too big, otherwise a relatively large amount of light will be lost. Every measurement point sees only the light of a single LED in the permissible angle range.

A better option for limiting the angle of illumination to conform to the standard geometry is to use the collimator lenses 12 mentioned above, which are disposed along every light-emitting diode-row source and are preferably physically grouped in lens arrays (several lenses made from an integral plastic part).

Every collimator lens 12 of a lens array collimates the light of mainly one light-emitting diode 11 (or, if using a lot of small light-emitting diode chips, of a spatially limited array of several light-emitting diode chips). The focal distances of the collimator lenses 12 are selected so that the divergence angle and the peripheral angle of the illumination of the measurement field in the longitudinal direction of the light-emitting diode row (y direction) are smaller than +/−10°. This produces an overlap within the illuminating strip 15 and results in a homogeneous distribution of lighting intensity. The screening plates 219 between the light-emitting diodes 11 mentioned above prevent light from a light-emitting diode reaching the measurement object via lenses of a neighboring light-emitting diode.

It is sufficient to use cylindrical lenses for the collimator lenses 12, which collimate the light beams in the longitudinal direction of the light-emitting diode row. The light-emitting diode row light source has a limited extension in the direction perpendicular to the row so that it satisfies the requirements stipulated for the standard geometry in this dimension, even without additional optics. Furthermore, the slot diaphragm 13 limits the width of the illuminating strip 15.

A measurement object, especially a printed sheet, must be measured without contact. The support surface for the sheet is not perfectly flat across the relatively large sheet surface as a rule. During scanning, this therefore results in variations in the distance between the measurement object and the measuring device. These must not be allowed to affect the measurement values. Accordingly, the lighting optics and measuring optics must not be dependent on distance beyond the tolerated range of a couple of tenths of a millimeter.

The lighting system illuminates beyond the visual field of the measuring optics (optical array 31) (the illuminating strip 15 is wider than the width of the scan line 16 detected by the optical array 31). Since the detection angle of the optical array 31 must be very limited (in accordance with the color measuring standards, detection angles of +/−5° only are tolerable), the light or beam density is measured by the optical array in the measurement field, which is not dependent on distance. The lighting system must therefore generate only a constant illumination intensity irrespective of the distance.

A concept whereby illumination can be applied at less than 45° irrespective of distance is already known and involves disposing a radiation source with a Lambert emission characteristic parallel with the plane of the measurement field. The position of the radiation source relative to the measurement field is selected so that the light hits the measurement field at an angle of 45°. In accordance with the photometric law, such lack of sensitivity to distance is achieved for a range of distance variations that is sufficient for the practical application. This concept, which is known per se, may be seen in FIG. 4 and may also be applied to this invention.

As mentioned above, in order to measure the measurement object in several color channels, the measuring device MD is equipped with several configurations illustrated in FIG. 4. These configurations (light sources 11, collimator lenses 12, slot diaphragm 13, line sensor 21, color filter 22, linear optical array 31) are disposed parallel with one another at a slight mutual distance apart (in the x direction) and differ solely due to different color filters 22.

The linear optical arrays 31 and the line sensors 21 of the individual color channels are offset from one another in the x direction. Consequently, each of the line sensors 21 receives measurement light at a given instant from different image element lines 16 of the measured object S extending in the y direction. By moving the measuring carriage MC and hence the measuring device MD across the measurement object S in the x direction, however, measurement light from all the image element lines 16 of the measurement objects S is applied to all the line sensors 21 sequentially in time. If the measuring device MD is fitted on a printing machine, the relative movement between the measuring device and measurement object is obtained by feeding the printed sheet under the measuring device.

It goes without saying that with an increasing number of color channels (on line sensors sensitized to different wavelength ranges) and a simultaneously decreasing bandwidth of the wavelength ranges, the more precise the color measurement which can be obtained will be. With 14-16 color channels at a distance of 20 nm each, the spectral resolution is the same as that of conventional spectral measuring heads. However, with an increasing number of color channels, the structural complexity of the system is also more complex and the computing resources for processing the measurement values is also increased. Conversely, with too low a number of color channels, it is no longer possible to obtain a color measurement that is precise enough for the intended purpose. An optimum comprise as regards measuring accuracy and manufacturing costs in terms of one aspect of the invention is to provide 6-12 color channels in the visible range plus possibly one additional channel in the near infrared range.

FIGS. 1-4 illustrate a preferred embodiment of the scanning device. For the purposes of this invention, however, other measuring configurations would also be suitable. For example, only one spectral measuring head may be provided in the measuring carriage MC. The image measuring unit may be integrated directly in the printing machine, for example in the known "web-inspection" systems. Alternatively, the measuring carriage may contain only the image measuring unit or—equivalent—the image measuring unit is integrated in the printing machine and an external manual measuring device is used as the spectral measuring head. The advantage of the first of the two arrangements is that the measurement can be conducted on a fully automated basis with the two units. With the latter arrangement, the printer must take the measurements manually with the external device, which is time-consuming and susceptible to errors.

The measuring sequence for the preferred scanning device illustrated in FIGS. 1-4 will be described below. A corresponding measuring sequence may be implemented in a similar manner for the other scanning devices or scanning configurations.

The printer places a printed sheet on the support surface underneath the measuring beam and activates the image measurement. The measuring beam is moved across the master sheet. As this happens, the master sheet is fully or partially measured by the image measuring unit. The image measurement values (the entirety of the measurement values of all the image pixels of the printed sheet) detected by means of the image measuring unit without polarization filters are converted into reflectance values using the device color calibration and stored in an external computer C, for example. Preferably still during the measuring routine, the spectral measuring head is guided in a defined manner to reference measuring points and measures these with and without polarization filters 301. The reference measurement points are preferably the fields of the color measuring strip CMS on the printed sheet S. If there is no color measuring strip on the sheet, the spectral measuring head is moved to pre-defined positions in the image and measures these with and without polarization filters. The reflectance spectra detected by the spectral measuring head with and without polarization filters at the reference measuring points are used as reference values and are also stored in the computer C.

In the configuration where the image measuring unit is integrated in the printing machine, the measurement data is detected from several printed sheets directly during the printing process and the corresponding measurement values forwarded to the external computer. When the printer draws a sheet along and measures the color measuring strip of the sheet with the spectral measuring head on an automated basis or manually, corresponding reference measurement values are generated for the correction. They correspond to the current state of the printing machine. For a better evaluation, the image measurement values may be determined on the basis of all the sheets stored in a corresponding period.

The advantage of the special scanning device illustrated in FIGS. 1-4 is that the spectral measuring head 300 generates reference values for correcting the image measurement values on the same measurement object and simultaneously with the image measuring process. This means that precise correction values (correction parameters) can therefore be determined for every print medium. The accuracy is significantly improved compared with a method which operates on the basis of pre-defined values only. The multiplicity of different printing materials (substrates, paper qualities) no longer imposes any limitation. Furthermore, the correlation between the time of the measurement and the drying process for the ink is eliminated. The influence of fluorescence due to different values of optical brighteners in the substrate or due to luminescent inks in the color coating can be corrected. Another aspect is the fact that the correction values are calculated automatically. The printer no longer has to select a paper quality manually when defining the printing parameters, which reduces susceptibility to errors.

In order to calculate the correction parameters used in the correction method proposed by the invention, which will be explained below, it is necessary to have at least reference values for a paper whiteness measurement and a measurement on a printed sample (reference measuring point) with a high density taken by the spectral measuring head with and without polarization filters. Furthermore, the same measurement fields or measurement points must be measured by the image measuring unit. However, the entire color measuring strip is advantageously measured by the spectral measuring head and the image measuring unit so that reference values for every color in the printing machine are available in full tone and as a halftone value. Further details will be given below.

When measuring the measurement object or printed sheet with the image measuring unit on the basis of image pixels, the measurement result is affected by various influencing variables, as explained above. These influencing variables are, for example, variances in the measuring geometry of the image measuring unit from the standard geometry, properties/structure of the surface of the measurement object and under certain circumstances the presence of optical brighteners in the print medium (fluorescence effects). However, the absence of polarization filters is also regarded as an influencing variable insofar as a different measurement result is obtained when measurements are taken using polarization filters.

The correction method proposed by the invention for the image measurement values determined by the image measuring unit is quite generally intended to compensate as far as possible or eliminate the effect on the measuring process of one or more of these influencing variables. More specifically, this means that the corrected image measurement values obtained as a result of the correction should be as close as possible to image measurement values measured under conditions at which the influencing variables do not exist or can have no effect. For the specific situation of the filter problems which occur using polarization, therefore, the correction proposed by the invention is intended as a means of calculating, from the image measurement values measured without polarization filters, corrected image measurement values corresponding to image measurement values measured with polarization filters.

In the case of the described spectral measuring head 300 with standard geometry and annular illumination, the influencing variable of measuring geometry is absent. If the spectral measuring head is used with polarization filters, the influencing variable of lack of polarization filters is also absent. The influencing variable of surface properties of the print medium also has no effect. The spectral measuring head is therefore ideally suited as a reference measuring unit.

The image measurement values are also converted or corrected in the external computer, for example.

The correction proposed by the invention is advantageously run in two steps and although each step already leads to an improvement, the combination of the two steps is optimal and therefore preferred.

In the first correction step, the image measurement values and the reference values of the spectral measuring head are adapted to one another without polarization filters and the medium-induced influence of the directional dependency and the measuring geometry eliminated. The measurement values are therefore optimally adapted to measurement values of the type measured by a color measuring device conforming to standard without polarization filters. This step may also include a fluorescence correction if necessary, if the spectral individual measuring head and the image measuring unit have different illuminating light sources.

In a second correction step, the image measurement values (determined without polarization filters) are then converted to measurement values which correspond to measurement values obtained by a measurement with polarization filters. These measurement values will be referred to as polarization filter (image) measurement values below.

Figure 5:
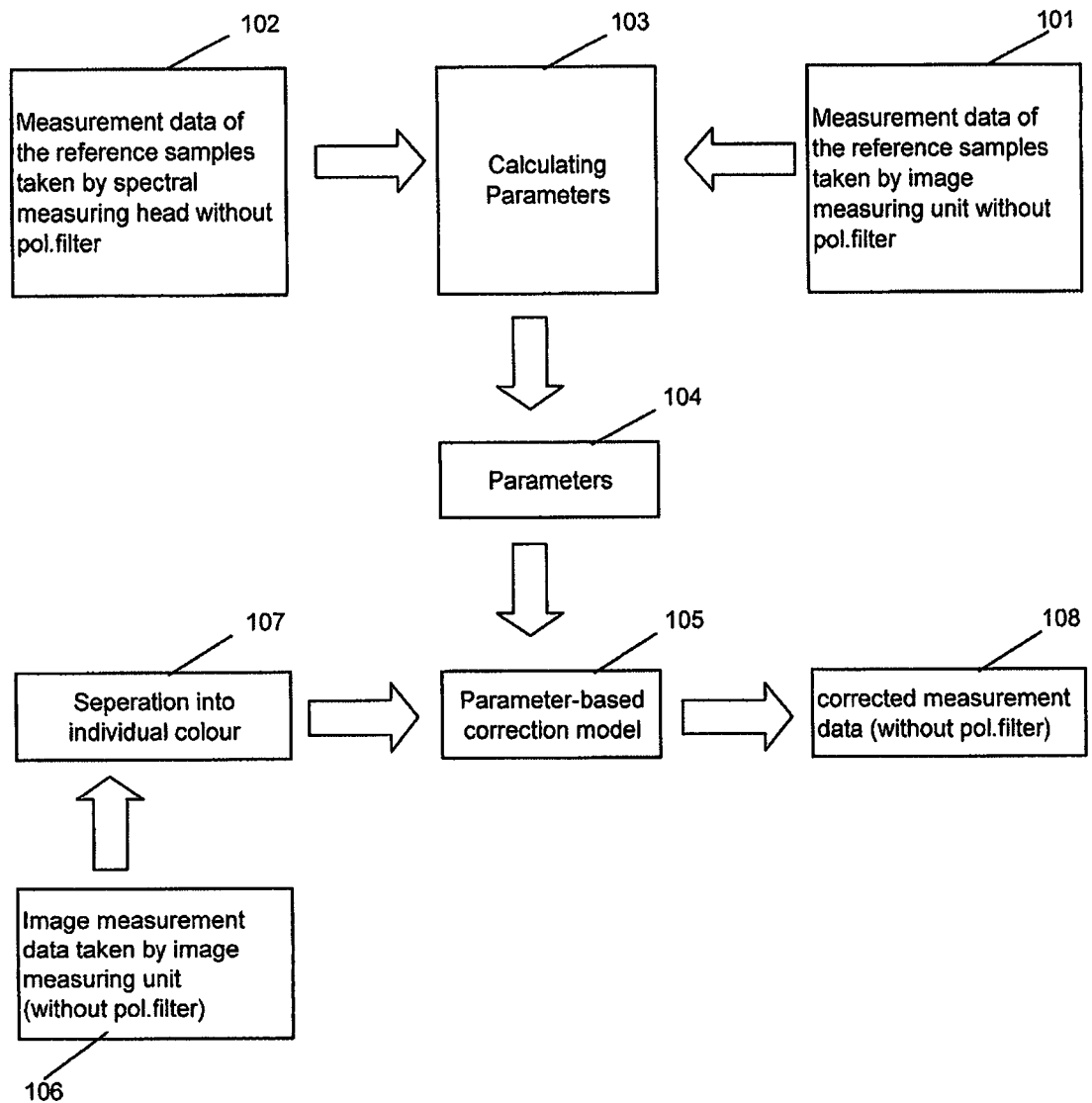
FIG. 5 is a flow chart illustrating how the measurement data is corrected with respect to the effects of medium and measuring geometry as well as the effects of fluorescence using a parameter-based model proposed by the invention.

The sequence of the first correction step is schematically illustrated in FIG. 5. The reference values measured on the color measuring strip or other appropriate reference fields (without polarization filters) by the image measuring unit and the spectral measuring head are available in the computer and are symbolized by blocks 101 and 102 in FIG. 5. In a parameter-based calculation stage 103, correction parameters 104 are determined from the reference values 101 and 102 of the image measuring unit and the spectral measuring head and forwarded to a correction model 105. It corrects the image measurement values measured (without polarization filters) from the image contents of the printed sheet by the image measuring unit (block 106) after previously separating them into individual colors (block 107) for every image measuring point and thus converts them into medium-corrected and geometry-corrected image measurement values 108, which are stored in the computer. The calculation of the correction parameters 104 and the correction 105 of the image measurement values are run automatically with every measurement.

The correction model 105 may be configured in varying degrees of complexity. A simple correction model permitting a meaningful improvement uses two parameters: an offset adaptation and a scaling factor. The scaling factor is a constant value for correcting the influences of measuring geometry. In order to correct the effects of fluorescence, the scaling factor is used as a characteristic curve function which is dependent on the measured reflectance value and spectrally dependent in the range of the fluorescence excitation.

Figure 6:
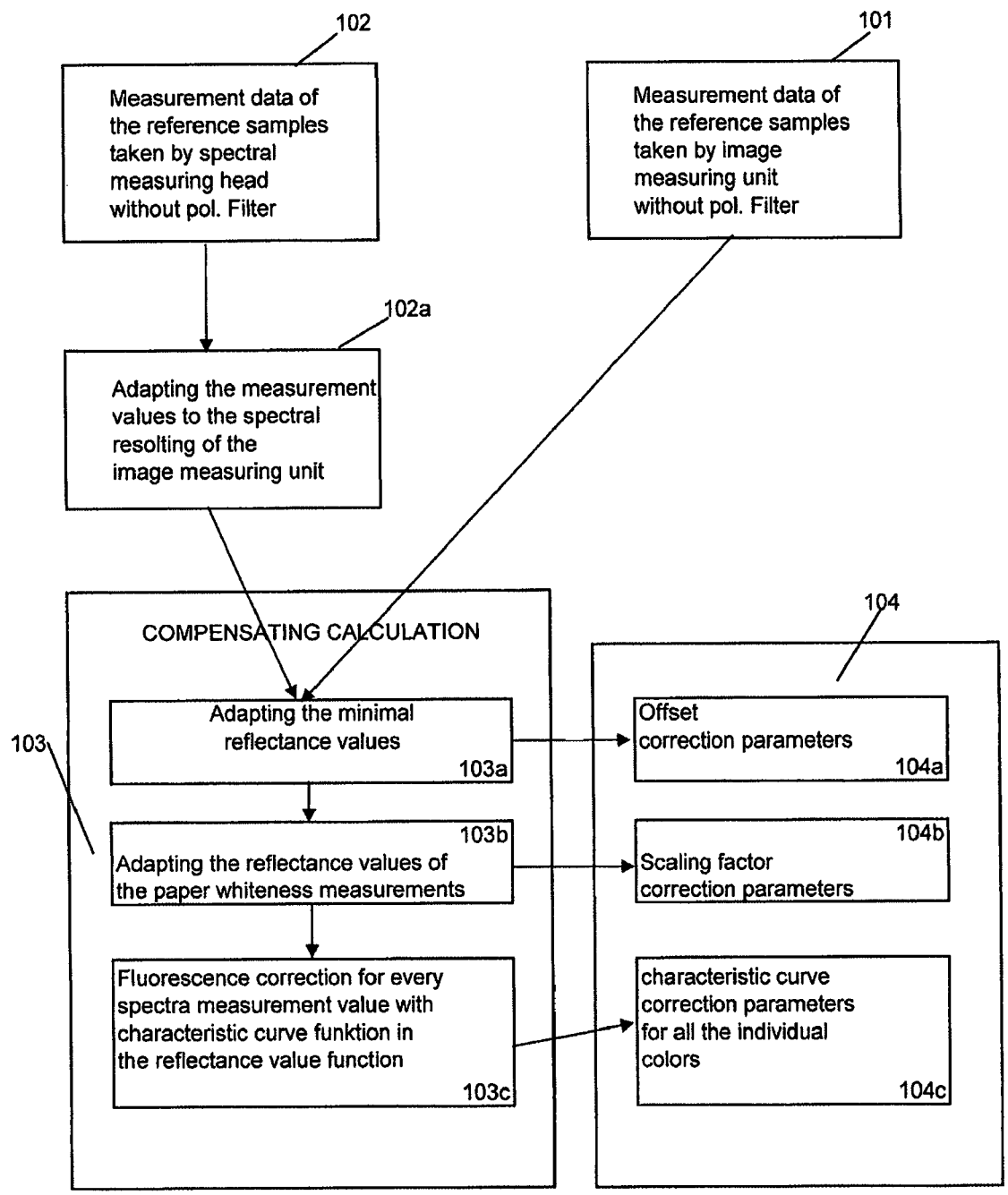
FIG. 6 is a flow chart illustrating how the correction parameters for correcting influencing variables caused by medium and measuring geometry are determined.

FIG. 6 schematically illustrates how the correction parameters are determined for the medium-dependent and measuring geometry influencing variables as well as the effects of fluorescence for non-polarized measurement values. The sequence will be described more specifically below.

As explained with reference to FIG. 5, reference values 101 measured from the color measuring strip or other appropriate reference points (without polarization filters) by the measuring unit and the reference values 102 of the spectral measuring head are used as the starting point. If the image measuring unit delivers measuring results with a lower spectral resolution than the spectral measuring head, the reference values 102 of the spectral measuring heads are adapted to the spectral resolution of the reference values 101 of the image measuring unit. This can be done by a process of averaging over the wavelength interval of the corresponding image measurement values. The weighting may also be obtained by means of a spectral evaluation function, which corresponds to the known normal observer function for CIE XYZ or the evaluation functions for tristimulus values or density filters, for example. The spectral resolution adaptation, which may be necessary, is symbolized by block 102a in FIG. 6.

The reference values 101 of the image measuring unit and the reference values 102 of the spectral measuring head, which may or may not have been spectrally adapted, are forwarded as input variables to the parameter calculating stage 103. It contains the correction model mentioned above and a compensating calculation using the reference values as input variables and the correction parameters to be calculated as variables.

The correction model itself is broken down into several sections. It comprises an offset adaptation, scaling and optionally a fluorescence and color coating correction.

In the offset adaptation, an offset value is subtracted from all the measurement data of the image measuring unit. In order to determine the offset value, the difference between the reference values 101 and 102 from high-density reference fields is determined and averaged. The mean value determines the offset value. This operation is shown by block 103$a$ in the drawing and the resultant offset value or offset correction parameter is denoted by reference 104$a$.

During the subsequent scaling operation, all the (offset adapted) image measurement values are multiplied by a scaling factor. The scaling factor is determined from the ratio of the two paper whiteness measurements (block 103$b$). A mean scaling factor across all the spectral measurement values is calculated as the scaling factor-correction parameter 104$b$ for the correction.

When the parameter-based correction model is applied later, the offset value is firstly subtracted from all the measurement data of the image measuring unit, after which all the image measurement values are multiplied by the scaling factor. In this respect, care must be taken to ensure that no values outside the physically valid rage occur. If such is the case, the calculated values are limited to the valid range.

If the two measuring systems (image measuring unit and reference measuring unit or spectral measuring head) do not use suppression of the UV element in the illuminating light, allowance must also be made for the effects of fluorescence caused by the different excitation of optical brighteners in the substrate. These effects are specific to the medium and can be characterized with the scanning device illustrated in FIGS. 1-4 and eliminated. This correction of the fluorescence effects is advantageously run in the first correction stage.

For a simple, industrially applicable model, the fluorescence correction can be integrated in the scaling factor for the adaptation to paper whiteness. In this case, however, a common constant correction value for all spectral wavelengths is no longer sufficient. The correction must be applied differently for each spectral measurement value in the active range of the fluorescence emission. For the optical brighteners, this corresponds to the spectral measurement values in the wavelength range of from 420 nm to 550 nm.

The spectral-dependent scaling factors are calculated by dividing the reflectance values from the paper whiteness measurements taken with the spectral measuring head and the image measuring unit in the active wavelength range of the fluorescence excitation.

In addition, allowance must be made for the influence of the color coating above the substrate. This requires an additional non-linear characteristic curve correction for every spectral supporting point in the active wavelength range. The characteristic curve correction corresponds to the multiplication of the spectral scaling factors by paper whiteness with an additional factor which depends on the measured reflectance value at the respective spectral supporting point. The characteristic curve can equally be applied as a function of the reflectance value or the halftone value. The characteristic curve correction may be applied in the form of a power function F $$F=(R)^\gamma,$$

for example, where R stands for the normalized reflectance value and $\gamma$ for the correction parameter.

Alternatively, the characteristic curve function may also be described by a polynomial approximation:

$$F=c_0+c_1*R+c_2*R^2+c_3*R^3+\ldots$$

where c0, c1, c2, c3, . . . represent the correction parameters.

The correction parameters are determined by means of a compensating calculation based on the reference measurement values 101 and 102 that is known per se. The compensating calculation is run and the correction parameters are calculated so that the correction values corrected by the correction model (having applied the parameters) match the reference values 102 as far as possible, e.g. using the known method of the smallest quadratic error. This part of the parameter calculation is symbolized by block 103$c$ in FIG. 6 and the corresponding characteristic curve correction parameters are denoted by reference 104$c$.

The compensating calculation used to calculate the correction parameters is run using the measurement values of the paper whiteness, from at least one halftone value with a not too high surface coverage (<=40%) and from a full tone measurement for every individual color. If no measurement values of halftone fields are available, a pre-defined typical characteristic curve may be used, which describes the relative curve between the paper whiteness measurement and full tone measurement.

If the color structure in an image measurement is known, the characteristic curve correction of the measurement value at a point in the image is calculated as the weighted mean value of the correction parameters of every color. The weighting corresponds to the coefficients of surface coverage of the color in the color structure of the sample.

The color structure at a point of the image may be known from the data of the preliminary stage or may be determined on the basis of known methods. In the case of four-color printing, Neugebauer's theory may be used. (Hans E. J. Neugebauer "Die theoretischen Grundlagen des Mehrfarbendrucks" Zeitschrift für wissenschaftliche Photographie, Photophysik und Photochemie, 36, 1937 ["The theoretical principles of multi-color printing", Journal of Scientific Photography, Photophysics and Photochemistry]). This being the case, the black element may be determined by a measurement value in the near infrared range.

If the color structure is not known, the correction parameters are determined from the mean values of the correction parameters of the different individual colors used for the conversion of all the measurement values.

Alternatively, a fluorescence correction may also be run using a physical model. The Kubelkà-Munk model with Saunderson correction for the surface effects describes the physical correlations when measuring a color coating on a scattering substrate. In this model, the coefficient of diffuse reflection of the substrate may be expressed by parameters in the function of the effective integral absorption in the UV wavelength range. One option is described in the dissertation by P. Emmel "Modéles de prédiction de couleurs appliquées a l'impression jet d'encre", thesis No. 1857 (1998) Ecole Polytechnique Fédérale de Lausanne [Prediction models for colors applied by inkjet printing]. Allowance may additionally be made for the influence of halftone fields using the method proposed by H. Neugebauer.

Figure 7:
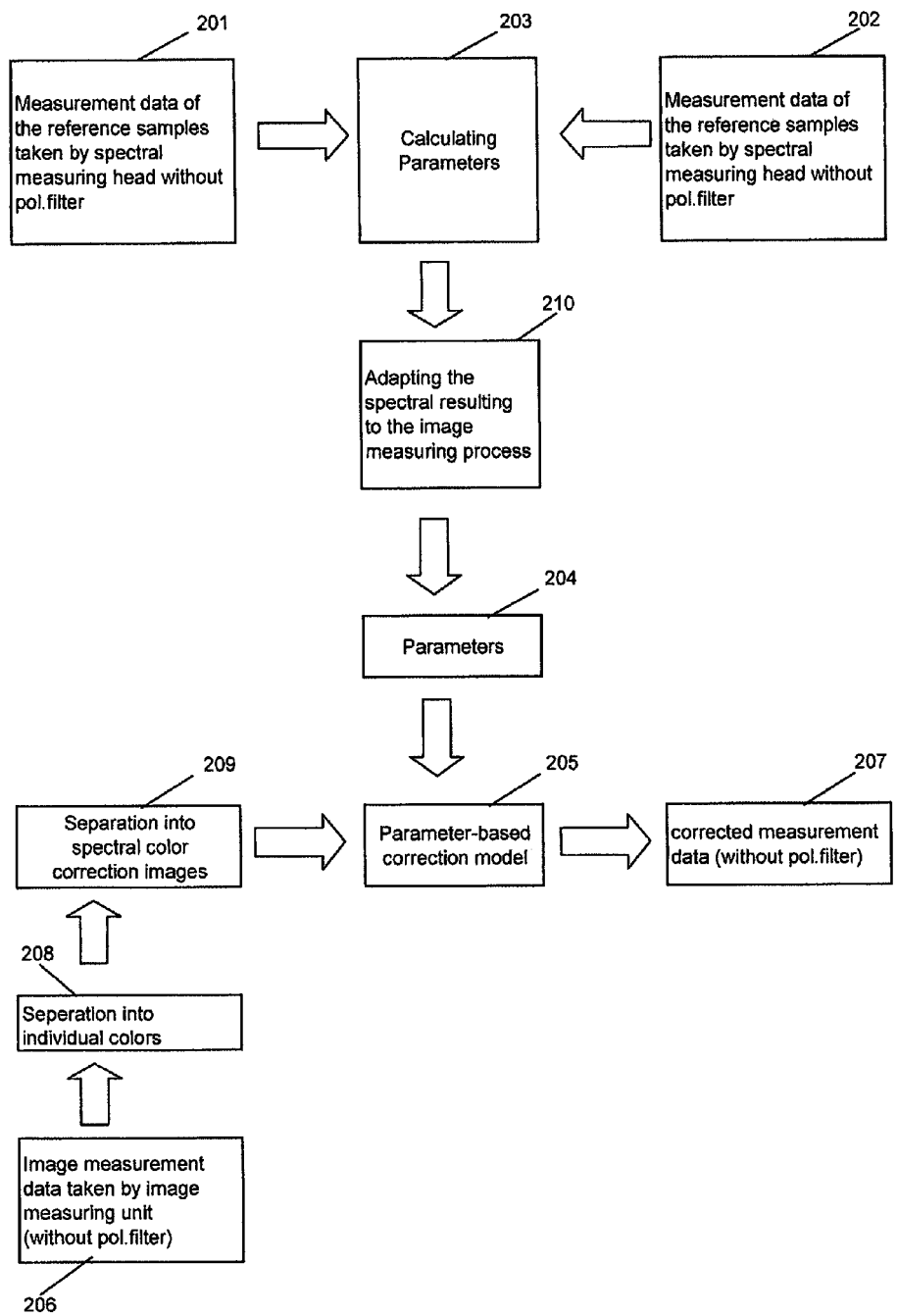
FIG. 7 is a flow chart illustrating the parameter-based model for converting the non-polarized image measurement values into polarized measurement values and FIG. 8 is a flow chart illustrating how the parameters of the parameter-based model for converting from non-polarized into polarized measurement values are calculated.

The second correction step is the transformation of the image measurement values without polarization filters into equivalent measurement values with polarization filters (polarization filter measurement values). For this transform (polarization filter conversion) the measurement values of every image pixel are transformed with a parameter-based model, the parameters of which are determined from the reference spectra measured by the spectral individual measuring head with and without polarization filters from selected image elements. The selected image elements are typically those of the color measuring strip CMS in the measurement object S. FIG. 7 illustrates these correlations.

Using the reference measurement data 201 and 202 measured by the spectral measuring head with and without polarization filters, parameters 204 for a correction model 205 are determined in a parameter calculation stage 203 and forwarded to the model. It then converts the image measurement data 206 (determined without polarization filters) of the image measuring unit into corresponding polarization filter measurement data 407. The parameters may be adapted to the spectral resolution of the image measuring unit in a stage 210 if necessary. The image measurement data 206 is separated into individual colors (block 208) and also into spectral correction ranges (block 209). The conversion into polarization filter measurement data 207 is run automatically with every measurement.

Figure 8:
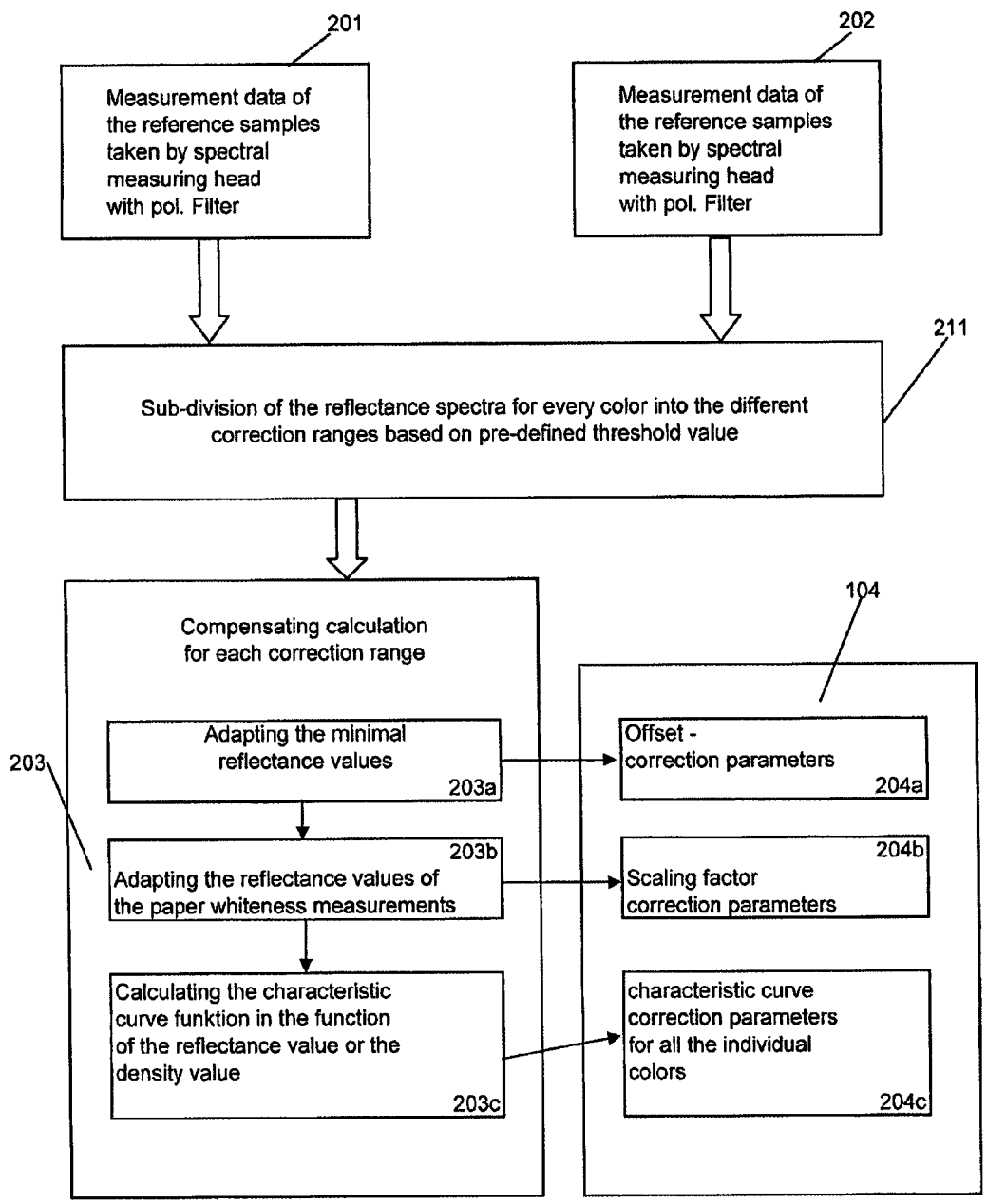

The calculation of the parameters of the parameter-based correction model 205 for converting the image data to account for the polarization filters is schematically illustrated in FIG. 8 and will be explained in more detail below.

The correction needed to obtain polarization filter measurement values is more complex than the correction explained in connection with FIGS. 5 and 6 relating to the medium-dependent and measurement geometry effects. For a colorimetric application, a special correction must be applied. A correction with a constant value for each color such as that used for converting the density values is not sufficient. Therefore, a spectral measuring head must be used for the reference measurements in order to determine the spectral correction parameters.

Allowance must be made for two physical effects in this correction. The first is the change in surface structure during the process of drying the color coating. Allowance for this change is made by means of an offset correction parameter in the model, which is subtracted from the reflectance values without polarization filters.

The second effect relates to the differing degree of depolarization of the measurement light scattered by the sample. The degree of depolarization varies significantly between the different substrate types. This component can be described with a scaling factor correction. The degree of depolarization is influenced by the spectral absorption of the color coating and this correction must therefore be run as a function of the spectral reflectance value or the spectral density with a characteristic curve function, in a manner similar to the fluorescence correction described above. Furthermore, in halftone printing methods, the characteristic curves behave differently in the absorption range and in the transmission range of a color spectrum. The correction is therefore specifically correlated to the color. The spectrum of each color is divided into at least two spectral ranges for which different correction factors are determined.

The reference measurement values of the color measuring strip determined previously with the spectral measuring head with and without polarization filters are available in the external computer for calculating the correction parameters in the parameter calculation stage; they are denoted by references 201 and 202. The reference measurement values contain full tone measurements and halftone measurements for every color and a paper whiteness measurement in both measurement modes.

Firstly, the reflectance spectra for each color are sub-divided into the different spectral correction ranges in a stage 211. The sub-division into absorption and transmission ranges can be run using a threshold value for the full tone spectra, for example a reflectance value of 0.2.

An offset correction parameter 204a is then determined for each spectral correction range. This value is determined by the difference in the reflectance values of the spectral measurement values with the highest density. Since the offset correction parameter is subtracted from the measurement without polarization filters, care must be taken to ensure that no over-correction resulting in negative measurement values occurs if there are higher densities in the image. If such a risk exists, only one reduced component of this differential value is used as the offset correction parameter. The corresponding calculation stage is denoted by reference 203a.

After the offset correction 203a, the paper whiteness spectra (for each spectral correction range) are adapted to one another by means of a spectral scaling factor. The scaling factor is obtained from the quotient of the reflectance values with and without polarization filters and is symbolized by reference 204b. The corresponding calculation stage is symbolized by block 203b.

In another step, characteristic curve correction parameters 204c are calculated for each spectral correction range in a stage 203c. The parameters for the characteristic curve in the absorption range are obtained as a function of the density value, i.e. as a function of the negative logarithm of the reflectance value. In the transmission range, the characteristic curve can be implemented as a function of the reflectance value or the density value. The characteristic curve function may be described on the basis of a power function or by a polynomial principle, as was the case with the fluorescence correction. The parameters of the characteristic curve function can be determined using the full tone, halftone value and paper whiteness measurement values using a compensation calculation. In the compensation calculation, the measurement values without polarization filters are incorporated in the characteristic curve function and evaluated. The aim of the optimization is to determine the parameter set which minimizes the quadratic differences from the reference measurement values with polarization filters.

The parameter set (all of the correction parameters in their entirety) is automatically determined every time a sheet is measured. If characteristic measurement values needed to determine the characteristic curve correction are missing, a previously determined typical characteristic curve is used.

For the conversion into polarization filter measurement values illustrated in FIG. 7, the correction parameter set 204 determined in this manner is transferred to the correction model 205 and applied to the image measurement values. If the image measurement values are not in spectral format, the spectral correction parameters are firstly determined from the corresponding spectral ranges of the individual image measurement values.

The color structure for every point of the image is then determined, i.e. which individual colors are used with which surface coverage. The color structure may be transferred from the data of the previous stage or calculated from the measurement values as described in connection with the fluorescence correction. On the basis of the color structure, the spectral correction parameters in the different spectral ranges are averaged on a weighted basis with the corresponding coefficients of surface coverage and applied to the image data in the same way as the parameter calculation. If the color structure is not available, a best mean value correction is determined for all the individual colors from the spectral correction parameter set for the correction model, which is then applied to all the measurement values.

The conversion into polarization filter measurement values proposed by the invention may also be run without a separate spectral measuring head if the image measuring unit is equipped with displaceable polarization filters. In this case, the whole printed sheet is measured by the image measuring unit without polarization filters. A polarization filter in the measuring device MD is then pivoted into the lighting and collection channel and only a part-region of the image is then measured with polarization filters in a separate, special scanning pass at an approximately 10 times slower scanning speed. This part-region advantageously contains the color control strip CMS or a part of the color measuring strip. Due to the lower scanning speed, the approximately 10 times longer measuring times (integration times) needed due to the loss of light when using polarization filters is achieved. In this case, the image measuring unit (fitted with polarization filters) itself is used as a reference measuring unit. The conversion parameters are determined and the measurement values converted in the same way as the method explained in connection with FIGS. 7 and 8, but using the measurement values taken by the measuring device MD with and without polarization filters from the selected part region of the image instead of the measurement values taken by the spectral measuring head. FIG. 4 symbolically illustrates a polarization filter denoted by reference 18, comprising two parts with intersecting polarization directions. The movement into the optical paths and out of the optical paths is symbolized by arrow 18a.

The invention claimed is:

1. A method of correcting image measurement values of a measurement object, comprising:
   (a) determining image measurement values by means of a photoelectrically operating image measuring unit on the basis of image pixels, whereby
   (b) converting the image measurement values measured by means of the image measuring unit by correction parameters of a parameter-based correction model into corrected image measurement values, wherein the corrected image measurement values do not contain at all or only at least partially contain the effects induced by at least one influencing variable, wherein the correction parameters used for the parameter-based correction model are determined from reference measurement values measured at selected reference measurement points by means of a reference measuring unit and the image measuring unit,
   wherein the reference measuring unit is used which is not susceptible to the at least one influencing variable or the latter has no or only a negligible effect on the measuring process.

2. The method according to claim 1, wherein the correction parameters are calculated by means of a compensating calculation contained in the correction model and the reference measurement values measured by the reference measuring unit and the image measuring unit are used as input variables and the correction parameters as variables, and the compensating calculation is run and the correction parameters determined so that the reference measurement values of the image measuring unit corrected by the correction model vary as little as possible from the reference measurement values of the reference measuring unit.

3. The method according to claim 1, wherein a measuring device operating on the basis of pixels with a measuring geometry which does not conform to the standard is used as the image measuring unit and the image measurement values are corrected with respect to the influence of the measuring geometry which does not conform to the standard, and the reference measuring unit used is the measuring device with the measuring geometry conforming to the standard.

4. The method according to claim 1, wherein the image measurement values are corrected with respect to the influence of fluorescence effects.

5. The method according to claim 1, wherein the image measuring unit used is a measuring device operating on the basis of pixels without polarization filters and the image measurement values are corrected with respect to the influence of the absence of polarization filters in the image measuring unit and thus converted into polarization filter image measurement values, for which purpose the measuring device with activatable polarization filters is used as the reference measuring unit.

6. The method according to claim 5, wherein reference measurement values are measured by means of the reference measuring unit at selected reference measurement points once with and once without polarization filters, and the correction parameters for the parameter-based correction model are determined using these reference measurement values measured with and without polarization filters.

7. The method according to claim 5, wherein spectral correction ranges are fixed and the image measurement values are assigned to these spectral correction ranges, and separate correction parameters assigned to each spectral correction range are calculated, and the image measurement values of every spectral correction range are corrected on the basis of the correction parameters assigned to the respective spectral correction range.

8. The method according to claim 6, wherein spectral correction ranges are fixed and the image measurement values are assigned to these spectral correction ranges, and the separate correction parameters assigned to each spectral correction range are calculated, and the image measurement values of every spectral correction range are corrected on the basis of the correction parameters assigned to the respective spectral correction range.

9. The method according to claim 1, wherein the image measurement values are corrected in two steps using a separate correction model in each case.

10. The method according to claim 8, wherein in a first step, the influence of the measuring geometry of the image measuring unit and if necessary fluorescence effects are corrected and in a second step, the image measurement values corrected in the first step are converted into polarization filter image measurement values.

11. The method according to claim 1, wherein the image measurement values are spectral measurement values.

12. The method according to claim 1, wherein during the calculation of the correction parameters, the spectral resolution of the reference measurement values measured by the reference measuring unit are adapted to the spectral resolution of the measurement values measured by the image measuring unit.

13. The method according to claim 3, wherein the parameter-based correction model incorporates an offset correction, scaling and a spectral characteristic curve correction.

14. The method according to claim 5, wherein the parameter-based correction model incorporates an offset correction, scaling and a reflectance-dependent or density-dependent characteristic curve correction.

15. The method according to claim 1, wherein the reference measuring unit used is a spectral measuring head with a measuring geometry conforming to the standard and insensitive to direction and has activatable polarization filters.

16. The method according to claim 1, wherein the image measuring unit and reference measuring unit used are respectively a measuring device with an illuminating light with no UV element.

17. The method according to claim 1, wherein a scanning device is used, which incorporates both the image measuring unit operating on the basis of pixels and the reference measuring unit.

18. The method according to claim 1, wherein the measurement object is a printed sheet.

19. The method according to claim 1, wherein the reference measurement values are measured by means of the reference measuring unit at the selected reference measurement points of the same measurement object once with and once without polarization filters, and the correction parameters for the parameter-based correction model are determined using these reference measurement values measured with and without the polarization filters.

* * * * *